US00PP29631P3

(12) United States Plant Patent
Hansen

(10) Patent No.: US PP29,631 P3
(45) Date of Patent: Aug. 28, 2018

(54) ***CORDYLINE* PLANT NAMED 'CHERRY CORDIAL'**

(50) Latin Name: *Cordyline fruticosa*
Varietal Denomination: Cherry Cordial

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 20 days.

(21) Appl. No.: 15/530,320

(22) Filed: Dec. 21, 2016

(65) Prior Publication Data
US 2018/0177100 P1 Jun. 21, 2018

(51) Int. Cl.
*A01H 5/12* (2018.01)

(52) U.S. Cl.
USPC ..... Plt./383
CPC ..... *A01H 5/12* (2013.01)

(58) Field of Classification Search
USPC ..... Plt./383
See application file for complete search history.

*Primary Examiner* — Keith O. Robinson

(57) ABSTRACT

A new cultivar of *Cordyline fruticosa* named 'Cherry Cordial' characterized by upright stems and compact foliage with irregular streaks of brown-purple to mahogany, bright cherry-red and olive-green in maturity on ovate leaves.

1 Drawing Sheet

Botanical classification: *Cordyline fruticosa.*
Cultivar designation: 'Cherry Cordial'.

BACKGROUND OF THE INVENTION

The present invention relates to a new and distinct cultivar of *Cordyline fruticosa* and will be referred to hereafter by its cultivar name, 'Cherry Cordial'. 'Cherry Cordial' represents a new cultivar of ti plant or palm lily and is grown as a foliage plant for landscape and indoor or outdoor container use. The inventor discovered the new cultivar as a single plant in a block of young plants derived from tissue culture of *Cordyline fruticosa* 'Chocolate Queen' (not patented) in Zeeland, Mich., USA in April of 2012.

Asexual reproduction of the new cultivar was first accomplished by shoot tip cuttings in September of 2012 at a wholesale nursery in Zeeland, Mich., USA under the direction of the inventor and has also been propagated since by sterile shoot tip tissue culture. The characteristics of this cultivar have been determined to be stable and are reproduced true to type in successive generations of asexual propagation.

No plants of *Cordyline* 'Cherry Cordial' have been disclosed or sold anywhere in the world, under any name, prior to one year of this application, except that which was obtained either directly or indirectly from the inventor.

SUMMARY OF THE INVENTION

The following traits have been repeatedly observed and represent the characteristics of the new cultivar. These attributes in combination distinguish *Cordyline* 'Cherry Cordial' as a new and different from all other cultivars of *Cordyline* known to the inventor:

1. Upright stems of compact foliage.
2. Leaf base color of brown-purple to mahogany.
3. Irregular streaked variegation of bright cherry-red and olive-green.

4. Foliage in denser shade develops more green and tan streaking.

In comparison to the parent plant 'Chocolate Queen', the new plant differs in having foliage that has irregular streaking of bright cherry-red and brown-purple to burgundy-colored foliage. 'Chocolate Queen' has marginal variegation with limited streaking in the leaf center and the variegation is of a creamy-white coloration in a medium green without the cherry-red, brown-purple to burgundy. The foliage under more shade becomes more green and tan striped and less bright cherry-red and olive-green. 'Cherry Cordial' can also be compared to the cultivar 'Willy's Gold' (not patented) but differs in having a mahogany-colored base rather than medium green, and the new plant develops a bright cherry-red streaking rather than the lighter pinkish-red. The cultivar 'BRA01' U.S. Plant Pat. No. 19,825 has similar dark foliage base but no streaking variegation. 'Katrijn' U.S. Plant Pat. No. 9,221 has variegation that is yellow-green and ivory when young and does not have the dark mahogany base of the new plant. 'Picolo' U.S. Plant Pat. No. 8,800 had variegation only on the margin and not the irregular streaking throughout with the mahogany base color. In comparison to the variety 'Ruby' (not patented), the new variety has an irregular streaking of bright cherry-red throughout the leaf rather than concentrated on the margin and displaying mostly on the new young foliage.

BRIEF DESCRIPTION OF THE DRAWING

The photographs of the two-year-old plant demonstrate the overall appearance of the plant, including the unique traits, grown in a greenhouse in Zeeland, Mich. The colors are as accurate as reasonably possible with color reproductions. Ambient light spectrum, source, direction and temperature may cause the appearance of minor variation in color.

DETAILED BOTANICAL DESCRIPTION OF THE PLANT

Figure 1:
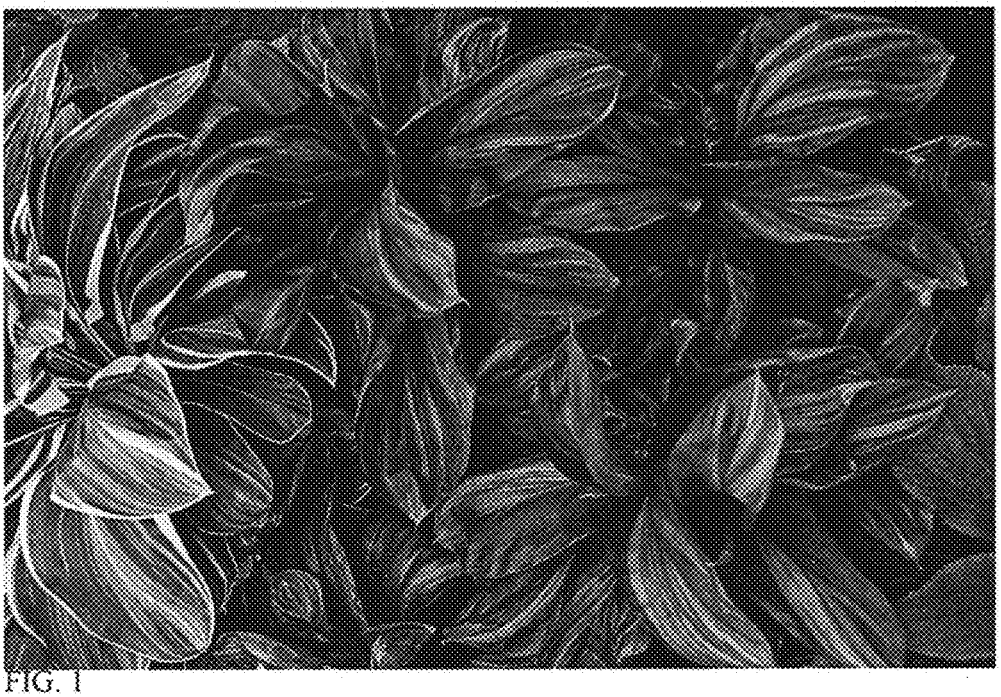
FIG. 1 shows the whole plant in the center of the photograph in comparison to leaves of the cultivar 'Chocolate Queen' on the left side of the photograph.
Figure 2:
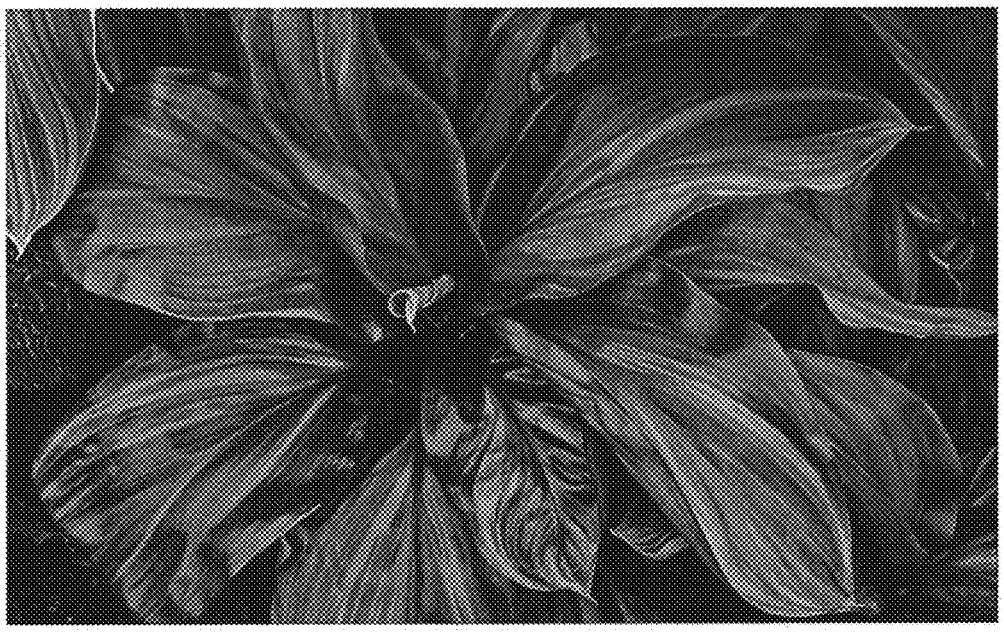
FIG. 2 shows a close-up of the foliage with irregular streaked variegation.

The following descriptions and color references are based on the 2001 edition of The Royal Horticultural Society Colour Chart except where common dictionary terms are used. The new plant, *Cordyline* 'Cherry Cordial', has not been observed under all possible environments. The phenotype may vary slightly with different environmental conditions, such as temperature, light, fertility, moisture and specimen maturity, but without any change in the genotype. The following observations and size descriptions are of a two-year-old plant in a geenhouse of a wholesale perennial nursery in Zeeland, Mich.

Parentage: Whole plant sport mutation of *Cordyline* 'Chocolate Queen';

Propagation method: By sterile shoot-tip tissue culture;

Growth rate: Rapid; finishing in a 65 mm liner in about three months from stage 3 rooted tissue culture plantlet;

Time to initiate roots: About 2 to 3 weeks in tissue culture;

Roots: Developing into fleshy roots about 2.5 mm diameter, not heavily branched; color dependent on soil, active roots typically nearest RHS 155D;

Habit: Upright frost-tender perennial with multiple stems from soil, becoming woody; with tightly-compact foliage; basal shoots absent;

Plant size: Average about 50.0 cm tall and 32.0 cm across about 35.0 to 40.0 cm above soil;

Stem: Base to about 1.5 cm diameter; glabrous; ridged from leaf scars;

Stem color: Blend between RHS 197C and RHS 199D;

Leaves: Ovate; acute apex; base acute to attenuate, aequilateral base; margin entire; glabrous abaxial and adaxial; glaucous abaxial and adaxial becoming lustrous; mostly flat with some coarse pleating along veins; curvature from distal to proximal ends weak;

Leaf size: Blade to about 20.0 cm long and about 10.3 cm wide, average about 18.0 cm long and about 8.5 cm across near longitudinal middle;

Leaf blade color: Young adaxial with streaks of irregular widths of nearest RHS N172A, RHS I87A, RHS N186C and between RHS 137A and RHS 183A with a margin about 1.0 mm wide nearest RHS N186C; young abaxial steaked with between RHS N187A and RHS 187A, nearest RHS N172A and RHS 178B with a margin about 1.0 mm wide nearest RHS N186C; mature adaxial streaked with irregular widths of nearest RHS 59B, RHS 168C with green tinting of nearest RHS 137C, RHS 139A and RHS 153A; mature abaxial nearest RHS 189A or darker;

Veins: Parallel; glabrous both abaxial and adaxial; abaxial midrib costate;

Vein color: Abaxial midrib base between RHS 53B and RHS 53C; lateral abaxial veins nearest RHS N186A;

Petiole: Short, concavo-convex; base clasping; margin entire; glabrous abaxial and adaxial; cross section strongly concave;

Petiole size: To about 7.0 cm long and 8.0 mm across at base, average about 5.5 cm long and 7.0 mm across;

Petiole color: Abaxial midrib nearest RHS 187C and border nearest RHS N187A; adaxial midrib and border nearest RHS 187A;

Flowers: Not observed; no flower production has yet been produced;

Hardiness and disease resistance: The new plant is not known to be able to tolerate temperatures below 0 degrees Celsius; Cherry Cordial is not known to be resistant beyond that typical of other *Cordyline fruticosa* cultivars. The new plant has not been extensively tested for disease tolerance or resistance. No resistance or tolerance to any disease is therefore claimed.

It is claimed:

1. A new and distinct cultivar of *Cordyline* plant named 'Cherry Cordial' as herein illustrated and described.

* * * * *